United States Patent [19]

Panster et al.

[11] Patent Number: 5,132,337

[45] Date of Patent: Jul. 21, 1992

[54] PASTY DENTAL MATERIAL

[75] Inventors: Peter Panster, Rodenbach; Ralf Janda, Bad Homburg; Peter Kleinschmit, Hanau, all of Fed. Rep. of Germany

[73] Assignee: Degussa Aktiengesellschaft, Frankfurt am Main, Fed. Rep. of Germany

[21] Appl. No.: 513,281

[22] Filed: Apr. 20, 1990

[30] Foreign Application Priority Data

Apr. 22, 1989 [DE] Fed. Rep. of Germany ....... 3913250

[51] Int. Cl.$^5$ .............................................. A61K 6/093
[52] U.S. Cl. .................................... 523/117; 523/113; 523/115; 523/116; 523/118; 524/443; 525/479
[58] Field of Search ............... 523/113, 115, 116, 117, 523/118; 524/443; 525/479

[56] References Cited

U.S. PATENT DOCUMENTS

| | | | |
|---|---|---|---|
| 3,926,906 | 12/1975 | Lee et al. | 524/786 |
| 4,504,231 | 3/1985 | Koblitz et al. | 523/117 |
| 4,575,545 | 3/1986 | Nakos et al. | 525/479 |
| 4,690,986 | 9/1987 | Sasaki et al. | 525/479 |
| 4,717,599 | 1/1988 | Merrill | 427/387 |
| 4,728,709 | 3/1988 | Klemarczyk et al. | 525/479 |
| 4,826,893 | 5/1989 | Yamazaki et al. | 525/479 |
| 4,853,434 | 8/1989 | Block | 525/100 |

FOREIGN PATENT DOCUMENTS

| | | |
|---|---|---|
| 2458380 | 6/1975 | Fed. Rep. of Germany . |
| 2403211 | 7/1975 | Fed. Rep. of Germany . |
| 3247800 | 7/1983 | Fed. Rep. of Germany . |
| 3610804 | 10/1986 | Fed. Rep. of Germany . |
| 3903407 | 8/1990 | Fed. Rep. of Germany . |

OTHER PUBLICATIONS

Ralf Janda, "Der Stand der Entwicklung auf dem Gebiet der Zahnfeullungskunststoffe (I)," *Die Quintessenz*, Jun. 1988, pp. 1067–1073.

Ralf Janda, "Der Stand der Entwicklung auf dem Gebiet der Zahnfuellungskunststoffe (II)," *Die Quintessenz*, Jul. 1988, pp. 1243–1253.

Ralf Janda, "Der Stand der Entwicklung auf dem Gebiet der Zahnfuellungskunststoffe (III)," *Die Quintessenz*, Aug. 1988, pp. 1393–1399.

*Chemical Abstracts*, vol. 100 No. 53364 M.

*Primary Examiner*—John C. Bleutge
*Assistant Examiner*—Karen A. Hellender
*Attorney, Agent, or Firm*—Beveridge, DeGrandi & Weilacher

[57] ABSTRACT

A pasty dental material, which hardens to a high-gloss polishable mass in the presence of an initiator, comprising a polymerizable bonding agent and a finely divided filler based on special heterosiloxanes.

9 Claims, No Drawings

PASTY DENTAL MATERIAL

INTRODUCTION AND BACKGROUND

The present invention concerns a pasty dental material, which hardens to a high-gloss polishable mass in the presence of an initiator, containing as the essential components a polymerizable bonding agent and a finely divided filler.

The dental material contains as a bonding agent at least one polymerizable acrylate or methacrylate and an optionally silanizable, novel filler based on polysiloxanes. It may also contain initiators to trigger polymerization, other fillers, such as finely ground glass types, highly dispersed silica or previously produced polymers, pigments and stabilizers. Other additives such as softeners or impact strength improvers may also be included in the dental material.

The term "dental material" as used herein comprises e.g. filling materials for carious defects or other dental defects in the mouth, inlays, crown and bridge materials, veneers, sealing and protective coatings, plastic adhesives to fix inlays or crowns and bridges, stump build-up materials, denture materials as well as masses for the production of artificial teeth Standard dental masses of the above mentioned type contain at least one monomeric ester of methacrylic acid, but in most cases a mixture of several of such esters. Suitable monofunctional esters of methacrylic acid are e.g. methylmethacrylate, ethylmethacrylate, isopropylmethacrylate, n-hexylmethacrylate and 2-hydroxyethylmethacrylate.

Recently, multi-functional esters of methacrylic acid with a higher molecular weight have also been used frequently, such as ethylene glycol dimethacrylate, butandiol1,4-dimethacrylate, triethylene glycol dimethacrylate, dodecandiol-1,12-dimethacrylate, decandiol-1,10-dimethacrylate, 2,2-bis-[p($\gamma$-methacryloxy-$\beta$-hydroxypropoxy)phenyl]-propane, the diaduct of hydroxyethylmethacrylate and isophorondiisocyanate, trimethylolpropanetrimethacrylate, pentaerythritetrimethacrylate, pentaerythritetetramethacrylate and 2,2-bis[p($\beta$-hydroxy-ethoxy)-phenyl]-propanedimethacrylate (bis-GMA).

The materials for dental use may, depending on the application purpose, be hardened in different ways.

Dental filling materials are known to exist in the form of photo-hardening as well as self-hardening (autopolymerizing) masses. The photo-hardening masses contain photoinitiators such as benzoinalkylether, benzilmonoketals, acylphosphinoxide or aliphatic and aromatic 1,2-diketocompounds such as e.g. camphorquinone as well as polymerization accelerators such as aliphatic or aromatic tertiary amines (e.g. N,N-dimethyl-p-toluidine triethanolamine) or organic phosphites, and harden when irradiated with UV or visible light.

The self-hardening materials comprise as a rule a catalyst paste and a base paste of which each contains a component of a redox system and which polymerize when the two components are mixed. One component of the redox system is in most cases a peroxide, such as e.g. dibenzoylperoxide, the other is in most cases a tertiary aromatic amine, such as e.g. N,N'-dimethyl-p-toluidine.

Other dental materials such as prosthesis plastics or plastic masses for the production of artificial teeth polymerize under heat application. The initiators in those cases are as a rule peroxides such as dibenzoylperoxide, dilaurylperoxide or bis(2,4-dichlor-benzoylperoxide).

All dental materials also contain as a rule pigments which--added in small amounts--act to match the color of the dental masses with the various shades of natural teeth. Suitable pigments are e.g. black iron oxide, red iron oxide, yellow iron oxide, brown iron oxide, cadmium yellow and orange, zinc oxide and titanium dioxide.

Dental materials further contain mostly organic or inorganic fillers in order to avoid a shrinking of the volume of the plastic mass during polymerization.

Pure monomeric methylmethacrylate for instance shrinks during polymerization by about 20 vol%. By adding ca 60 weight parts of solid methylmethacrylate-pearl polymer the shrinking may be reduced to ca. 5-6 vol% (see German Patent 24 03 211).

Other organic fillers are obtained by producing a polymer which consists essentially of esters of methacrylic acid and is either non-cross-linked or cross-linked. This polymer optionally contains surface-treated fillers. If it has been produced as a polymer it may be added to the dental material in this form; if on the other hand it was produced by solventless polymerization in compact form it must be ground into a so-called splinter polymer before being added to the dental material.

Frequently used previously produced polymers are in addition to the already mentioned filler-containing pearl and splinter polymers homopolymers of methacrylic acid methyl ester or, preferably non-cross-linked, copolymers of methyl methacrylate with a low content of esters of the methacrylic acid or acrylic acid with 2 to 12 carbon atoms in the alcohol component, best in the form of a pearl polymer. Other suitable polymers are non-cross-linked products based on polyurethanes, polycarbonates, polyesters and polyethers.

Inorganic fillers are e.g. ground glasses or quartz with average particle sizes between 1 and 10 $\mu$m as well as highly dispersed $SiO_2$ with average particle sizes between 10 and 400 nm.

The glasses are preferably aluminumsilicate glasses which may be doped with barium, strontium or rare earths (German Patent 24 58 380).

It should be noted in regard to the finely ground quartz or the finely ground glasses and the highly dispersed $SiO_2$ that the inorganic filler is as a rule silanized prior to the mixing with the monomers in order to achieve better bonding to the organic matrix. For this purpose the inorganic fillers are coated with silane coupling agents which in most cases have a polymerizable double bond for reaction with the monomeric esters of the methacrylic acid.

Suitable known silane coupling agents are e.g. vinyltrichlorsilane, tris-(2-methoxyethoxy)-vinylsilane, tris-(acetoxy)-vinylsilane and 3-methacryloyloxypropyltrimethoxysilane.

The initially mentioned, recently used monomers with higher molecular weight also result in a decrease of polymerization shrinkage. To these monomers the described, inert inorganic finely ground glasses or organic fillers mixtures thereof are added up to 85 wt%, which results a further reduction of the shrinkage to ca. 1 vol%.

The inorganic fillers not only result in a decrease in polymerization shrinkage but in addition in a significant strengthening of the organic polymer structure. This strengthening also shows itself in an improvement of mechanical characteristics and in an increase in wear resistance (R. Janda, Quintessenz 39, 1067, 1243, 1393 1988). Good mechanical characteristics and high wear resistance are important requirements which must be fulfilled by a dental compound which is intended as a long-term replacement for lost hard natural dental substance.

But in addition to strengthening characteristics the filling compounds also must fulfill other material parameters. An important parameter in this context is the polishability. High gloss polishability is of significant importance for filling materials and crown and bridge materials for at least two reasons:

A high-gloss and completely homogenous surface must be required of the filling material for aesthetic reasons, so that the filling cannot be distinguished from the surrounding, absolutely smooth, natural tooth enamel. This high-gloss filling surface also must retain its characteristic for a long period.

A highly smooth filling surface is also important so that plaque or discoloring media cannot attach themselves.

However, it has now been shown that the previously described finely ground quartz or glass fillers have good strengthening characteristics, but do not fulfill requirements in regard to their polishability. It has therefore been attempted to grind these fillers even finer in order to obtain more homogenous surfaces. However, physical grinding methods are limited, so that average grain sizes below 1 µm are hard to achieve.

When highly dispersed silicic acid (average particle size 10 to 400 nm) was used as a filler in dental masses (German Patent 24 03 211) it was surprisingly shown that these fillers were able to achieve a significant improvement in polishability. Disadvantages of the highly dispersed silica result from its greatly thickening effect, so that today, as a rule, filling degrees above 52 wt% cannot be obtained, unless insufficient processing technology characteristics are tolerated.

The materials filled with highly dispersed silica acid also showed clearly lower stabilities and hardness than those filled with quartz or finely ground glass.

SUMMARY OF THE INVENTION

It is an object of this invention to provide new photo-, heat- or selfhardening dental materials comprising a polymerizable organic bonding agent and a finely divided filler, which on the one hand may be polished to high gloss and thus fulfill the aesthetic requirements of a dental material, but which on the other hand have better physical characteristics than the dental materials representing the present state of technology.

In attaining the above and other objects, a feature of the invention resides in, a new pasty dental material, which hardens to a high-gloss polishable mass in the presence of an initiator, comprising a polymerizable bonding agent and a finely divided filler. The dental material contains as a filler a heterosiloxane which consists of units of the formula

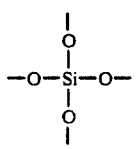

(I)

and units of the formula

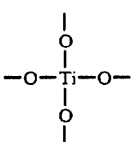

(II)

and may optionally also contain units of the formula

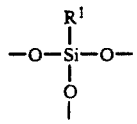

(III)

wherein $R^1$ stands for a linear or branched alkyl group with 1 to 18 carbon atoms, a cycloalkyl group with 5 to 8 carbon atoms, a phenyl group or an arylalkyl group or a linear, optionally branched alkyl group with 1 to 6 carbon atoms bonded with an acrylate or methacrylate residue, or a unsaturated linear, optionally branched hydrocarbon residue with 2 to 8 carbon atoms or a cyclic, single olefinic unsaturated hydrocarbon residue with 5 to 8 carbon atoms, and/or represents units of the formula

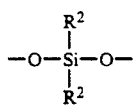

(IV)

wherein $R^2$ is a methyl, ethyl or phenyl group, and the free valences of the oxygen atoms bonded with the silicon or titanium atoms in the units (I) to (IV) are as in the silica structures saturated by a silicon atom of a same or different unit and/or by a titanium atom, whereby the ratio of the sum of the silicon atoms of the units of Formula (I), (III) and (IV) to the titanium atoms of the units of Formula (II) is 1:1 to 100:1 and the share of silicon atoms of the units (I) to the total amount of silicon atoms is 100 mol% to 30 mol%.

The units according to Formulas (I) to (IV) may naturally be present in different forms in respect to each other, i.e. they may be present in the form of a statistical copolycondensate or in the form of a block-copolycondensate or in the form of a so-called mixed copolycondensate. According to the invention the fillers of the new dental materials may in respect to the units according to Formulas (I) to (IV) be present in any of the mentioned forms and their mixtures. This means that in the case of a pure statistical copolycondensate which contains units of the Formula (I), (II), (III) and (IV) a pure statistical distribution of the components according to the molar ratios of the starting products is given. In the case of a so-called blockcopolycondensate blocks of identical units according to Formula (I), (II), (III) and (IV) form. Finally, a so called mixed copolycondensate possesses structures of a statistical copolycondensate as well as of a block-copolycondensate.

The fillers are used in the dental masses in an amount from 20 to 90 wt%, preferably 40 to 90 wt%.

A particularly advantageous filler composition which is characterized as being readily feasible uses a heterosiloxane as filler which consists only of the units of Formula (I) and (II) whereby the molar ratio of the units of Formula (I) to the units of Formula (II) is 3:1 to 100:1.

The fillers according to the invention naturally must—to the extent that there is no double bond functionality—prior to their addition into the organic polymer matrix be reacted with a suitable organosilane compound, preferably 3-methacryloyloxy propyltrimethoxy- or 3-methacryloyloxy propyltriethoxysilane. This does not preclude, however, that even double bond-functional fillers must still undergo additional silanization.

This applies analogously also for a filler composition according to the invention which is advantageous for reasons of being readily available because of the starting materials and in which the heterosiloxane is made up of units of Formula (I), (II) and the specific units of Formula (IV)

$$-O-\underset{\underset{CH_3}{|}}{\overset{\overset{CH_3}{|}}{Si}}-O-$$

whereby the molar ratio of the sum of units according to Formula (I) and (IV) to the units of Formula (II) is 1:1 to 100:1.

The monomeric elements of the fillers according to the invention are principally known compounds. A monomeric compound for a unit of Formula (I) is e.g.

$$Si(OC_2H_5)_4$$

for a unit of Formula (II) e.g.

$$Ti(OC_3H_7)_4$$

for a unit of Formula (III) e.g.

$$H_2C=\underset{}{\overset{\overset{CH_3}{|}}{C}}-\overset{\overset{O}{\|}}{C}-O-(CH_2)_3-Si(OCH_3)_3$$

or $$CH_3-CH_2-CH_2-Si(OCH_3)_3$$

and for a unit of Formula (IV) e.g.

$$(CH_3)_2Si(OC_2H_5)_2$$

The compositions of the dental filling materials that may be produced from them may be described e.g. by formulas for a particular polymer unit such as 30 SiO$_2$.TiO$_2$ 40 SiO$_2$.CH$_3$CH$_2$CH$_2$SiO$_{3/2}$.TiO$_2$ 20 SiO$_2$.CH$_3$CH$_2$CH$_2$SiO$_{3/2}$.TiO$_2$.(CH$_3$)$_2$SiO$_{2/2}$ 10 SiO$_2$.TiO$_2$.(C$_2$H$_5$)$_2$SiO$_{2/2}$ or $$SiO_2.TiO_2.CH_2=\overset{\overset{CH_3}{|}}{C}-\overset{\overset{O}{\|}}{C}-O-(CH_2)_3-SiO_{3/2}.$$

In view of the physical characteristics, the fillers of the composition according to the invention are particularly well suited for use in the dental materials if they have a specific surface of up to 200 m$^2$/g, preferably about 0 to 100 m$^2$/g, and a particle size from 0.01 μm to 100 μm, preferably from 0.1 μm to 30 μm.

DETAILED DESCRIPTION OF INVENTION

The fillers contained in the dental material according to the invention may be obtained according to various methods. One of these provides for making the filler available in the form of statistical polycondensate by dissolving an alkoxysilane of the general formula $$Si(OR^3)_4 \qquad (V)$$

whereby R$^3$ is a linear or branched alkyl group with 1 to 5 carbon atoms, and a titanium compound of the general formula $$Ti(OR^3)_4 \qquad (VI)$$

in which R$^3$ has the same meaning as in Formula (V), and optionally an alkoxysilane of the general formula $$R^1-Si(OR^3)_3 \qquad (VII)$$

wherein R$^1$ stands for a linear or branched alkyl group with 1 to 18 carbon atoms, a cycloalkyl group with 5 to 8 carbon atoms or an arylalkyl group or for a linear, optionally branched alkyl group with 1 to 6 carbon atoms bonded with a acrylate or methacrylate residue, or for a single olefinic unsaturated, preferably end-positioned unsaturated linear or branched hydrocarbon residue with 2 to 8 carbon atoms or for a cyclic, single olefinic unsaturated hydrocarbon residue with 5 to 8 carbon atoms, and optionally dissolving an alkoxysilane of the general formula $$R^2{}_2Si(OR^3)_2 \qquad (VIII)$$

in which R$^2$ is a methyl, ethyl or phenyl group and R$^3$ in Formula (VII) and (VIII) has the same meaning as in Formula (V) and (VI) in a mostly water-miscible solvent which, however, dissolves the compounds according to Formulas (V) to (VIII), and by adding to the solution while stirring an amount of water which is at least sufficient for the complete hydrolysis and condensation, then by precondensing the reaction mixture during continued stirring at a certain temperature ranging from room temperature to 200° C, by stirring the forming solid matter, optionally after addition of another solvent or water, for 1 to 6 more hours at 60° C to 200° C, at normal pressure or under a pressure which corresponds to the sum of partial pressures at the respective temperature, then post-treating the formed heterosiloxane, optionally after a change of the medium and/or pH value, for another 4 h to 5 days at 100° C to 250° C in the liquid phase, then separating according to standard methods from the liquid phase, optional washing, drying at room temperature up to 200° C, optionally in a controlled atmosphere or in vacuum, optional subsequent tempering for 1 to 100 hours at temperatures from 150° C to 300° C in a controlled atmosphere or in vacuum, optional grinding and/or classification according to size, whereby the heterosiloxane filler which has been separated from the liquid phase and optionally washed is treated prior to or after one of the phases of drying, tempering, grinding, classification in water, a water/alcohol mixture or in pure alcohol, in the presence of an acidic or basic catalyst, preferably in presence of ammonia, for a period of 1 hour to 5 days at temperatures from 60° C to 250° C under a pressure which corresponds to the sum of partial pressures at the respective temperature.

The advantageous application-technical characteristics of the new fillers are also based on the acidic or basic thermal treatment prior to or after the drying or in another of the optionally used treatment phases, since this results in particular in a strengthening of the polymer structure. A typical acidic catalyst is e.g. hydrochloric acid or acetic acid, while the typical basic catalysts are e.g. represented by ammonia or an amine.

As a principle, the corresponding halide or phenoxy compounds may be used in place of the alkoxy compounds as starting materials for the process. However, their use offers no advantages, but may, for example in the case of chlorides, result in problems because of the HCl released during hydrolysis.

The hydrolysis of the monomers must be performed with an essentially water-miscible solvent which, however, dissolves the starting materials. Alcohols which correspond to the alkoxy groups at the monomeric starting materials are preferred. Particularly suitable are methanol, ethanol, n-and isopropanol, n- and isobutanol and n-pentanol. Mixtures of such alcohols may also be used as solvents during the hydrolysis. It is naturally also possible to use other polar solvents which are essentially water-miscible, but this is not very logical for reasons of process technology because of the solvent mixtures produced with the hydrolytically separated alcohol.

The hydrolysis is preferably performed with an excess of water above the stoichiometrically required amount. The amount of water required for hydrolysis depends on the hydrolysis speed of the respective monomer in such a manner that with an increasing amount of water the hydrolysis speeds up. However an upper limit may be given through segregation and forming of a two-phase system. As a rule hydrolysis is preferred in a homogenous solution.

Because of the mentioned aspects, in practice that maximum amount of water (in weight) is used as is used overall at silane monomers.

The polycondensation may be performed at different temperatures. Since the polycondensation is fastest at higher temperatures it is preferably performed at reflux temperature or slightly below. In principle the hydrolysis and polycondensation, may still be performed at still higher temperatures than the reflux temperature, i.e. under pressure.

During polycondensation the reaction mixture may congeal into a solid mass. For this reason it is useful to add a corresponding amount of solvent or water for dilution.

As a rule, the solvent here will be the same as the one already used during hydrolysis of the silanes, i.e. preferably a lower alcohol with 1 to 5 carbon atoms.

As an alternative to the dilution with a solvent, it is naturally also possible to dilute with water. Whatever is used in the individual case depends on which physical characteristics are desired in the copolycondensate to be produced. This may also be influenced by the duration and temperature of after-treatment in the liquid phase or in dry form. An after-reaction at higher temperature always results in a strengthening of the polymer structure and in an improvement of the mechanical properties.

The separation of the formed solid matter may be performed according to standard methods, such as filtration, decantation, centrifugation or distilling off of the liquid phase. The washing of the formed solid matter is preferably performed with the solvent used during the separation or with water.

The dried or tempered product may be ground in the usual devices and may be classified into various particle size fractions. Depending on the circumstances, one or the other of the finishing measures washing, drying, tempering, grinding and classification may be foregone, or they may be performed in a different sequence.

A classification may e.g. also be performed at the wet product which may have been optionally dried or tempered before.

The duration of the hydrolysis depends on the hydrolysis suitability of the starting materials and on the temperature. The hydrolysis temperature depends in particular on the alkoxy groups located at the silicon whereby the methoxy group hydrolyzes fastest and the process is slowed down with increasing chain length or increasing branching.

Hydrolysis and polycondensation may be accelerated by addition of organic or inorganic bases, e.g. ammonia or amines, or organic or inorganic acids, e.g. hydrochloric acid or formic acid, or by the standard condensation catalysts, e.g. dibutyltin diacetate.

In order to compensate for different hydrolysis and polycondensation characteristics of the monomeric components of a statistical copolycondensate, the monomeric components according to Formula (V), (VI), (VII) and (VIII) may be precondensed according to one production version. For this purpose the monomeric components—with or without the use of a solvent dissolving the starting materials, preferably linear or branched alcohols with 1 to 5 carbon atoms corresponding to the alkoxy groups--are precondensed in the presence of an amount of water insufficient for complete hydrolysis, preferably 1 to 100 mol% of the amount required for it, for a period of 5 min to 5 days at room temperature to 200° C.

In order to promote this precondensation effect an acidic or basic condensation catalyst may be added to the process. Preferred catalysts are e.g. nitric acid, phosphoric acid, hydrochloric acid, acetic acid, ammonia, amines, soda lye or caustic potash solution or also a metal-containing catalyst, e.g. dibutyltin diacetate, which are used in gas form or dissolved in water or in an organic solvent.

After the precondensation has been performed the complete hydrolysis and polycondensation, after optional addition of further water and optional addition of further solvent, is performed as described.

According to a different method, so-called block copolycondensates are obtained in which blocks of identical units according to formula (I) and (II), (III) and (IV) have been formed. In this method the monomeric components according to Formula (V), (VI), (VII) and (VIII), respectively independent from each other, are precondensed with or without the use of a solvent dissolving the starting materials, preferably a linear or branched alcohol with 1 to 5 carbon atoms corresponding to the alkoxy groups, in the presence of an amount of water insufficient for complete hydrolysis, preferably 1 to 100 mol% of the amount needed for this, for a period of 5 min to 5 days at room temperature to 200° C, the obtained condensates are combined and then, after optional addition of additional water and/or optional addition of additional solvent, the complete hydrolysis and polycondensation is performed as described.

Naturally, it is also possible to use one of the above mentioned condensation catalysts in the production version according to the invention.

According to another method, so-called mixed copolycondensates are obtained in which a partial formation of blocks of identical units according to Formula (I), (II), (III) and (IV) is present, but in which at least one monomeric component is always present in the not precondensed condition and at least one monomeric component is present in a precondensed condition.

This method is characterized by precondensing from the monomeric components according to Formula (V), (VI), (VII) and (VIII) at least one monomer, but no more than 3 monomers, independent from each other, with or without use of a solvent dissolving the starting materials, preferably a linear or branched alcohol with 1 to 5 carbon atoms corresponding to the alkoxy groups, in the presence of an amount of water insufficient for complete hydrolysis, preferably in the presence of 1 to 100 mol% of the amount required for this, for a period from 5 min to 5 days at room temperature to 200° C, by combining the obtained precondensate or the obtained precondensates and at least one unprecondensed component with each other, and by then performing--after optional addition of additional water and/or optional addition of additional solvent--the complete hydrolysis and polycondensation as described.

The use of an acidic, basic and/or metal-containing condensation catalyst for precondensation is also feasible in this production version and the further treatment of the formed polycondensate takes place as in the other described production processes.

During the performance of the precondensation the amount of water used depends on the oligomerization degree to be obtained, i.e. which block size is to be attained. If more water and a longer precondensation time are used for precondensation this results naturally as a rule in larger units than if less water and a shorter reaction time are used.

The duration of the precondensation depends, as already described above, in general naturally also on the hydrolysis readiness of the monomeric components and on the temperature.

The fillers for the new dental materials are characterized in particular by the quantitative hydrolysis and condensation yield and elementary analyses. In purely optical respects there is no difference between the copolycondensate obtained according to the various production processes. Depending on the treatment the fillers according to the invention have surfaces of about 0 to 200 m²/g. The desired particle size diameters of 0.01 μm to 100μm may be set without difficulty by using standard grinding techniques.

Another object of the invention is the use of the dental materials for the production of dental fillings, inlays, dental sealants, coatings to protect tooth surfaces, crowns, veneers, bridges, dentures, artificial teeth, bonders for the attachment of inlays, crowns and bridges and for the building up of tooth stumps.

The invention is further explained by the following illustrative examples.

1. Preparation of filling materials to be used in accordance with the invention

EXAMPLE 1

1,404.2 g (6.74 mol) Si(OC$_2$H$_5$)$_4$ and 95.7 g (0.337 mol) Ti(i-OC$_3$H$_7$)$_4$ were combined in 200 ml of ethanolic HCl solution and first precondensed in a 3 l Woulff bottle (3-neck flask) with KPG agitator and reflux condenser for a period of 5 h at reflux temperature. After this time the solution was first diluted with 300 ml of ethanol and than reacted for 10 min with 525 ml of 10% ammonia solution. It was stirred for another 2 hours with reflux, then the mixture was cooled and the formed solid matter was filtered off via a suction filter and washed with 2 × 500 ml of water. The obtained solid matter was then transferred to a 3 l autoclave, 1 liter of 5% ammonia solution were added to it and it was stirred for 24 h at 150° C. After renewed filtering off, washing with 1 liter of water and 15 hours of drying at 120° C in N: atmosphere 429.0 g (99.3 % of theoretic Yield) of a dental filling material consisting of polymer units of the formula

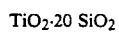
TiO$_2$·20 SiO$_2$ were obtained. The product was then ground for 24 h in a ball mill.

| Analyses: | % Ti | % Si |
|---|---|---|
| Theory: | 3.74 | 43.83 |
| Actual: | 3.70 | 43.40 |
| Specific surface: | 72 m²/g | |

EXAMPLE 2

1,426.0 g (6.845 mol) Si(OC$_2$H$_5$)$_4$ and 48.6 (0.171 mol) Ti(OC$_3$H$_7$)$_4$ were combined in 500 ml of isopropanol which was 1n in HCl. 1 ml H$_2$O was added to the solution and it was then stirred for 24 h with reflux. After that time 25.4 g (0.171 mol) of (CH$_3$)$_2$Si(OC$_2$H$_5$)$_2$ and 400 ml of water are added to the precondensate. After the solid matter formed, 750 ml of water were added for dilution and it was stirred another 2 h with reflux. It was subsequently cooled and the formed solid matter was filtered off and suspended in a 5% ammonia solution. The suspension was transferred to an autoclave and then stirred for 48 h at 130° C under built-up pressure. After cool-down, filtering off of the solid matter, washing with 2 l of water, 10 h of drying at 120° C and 12 h tempering at 160° C in N: atmosphere 434.9 g (99.2 % of theoretical yield) of a dental filling material consisting of units of the formula

TiO$_2$·(CH$_3$)$_2$SiO$_{2/2}$·40 SiO$_2$ were obtained. The product was then ground for 24 hours in a ball mill.

| Analyses: | % C | % H | % Si | % Ti |
|---|---|---|---|---|
| Theory: | 0.94 | 0.24 | 45.03 | 1.87 |
| Actual: | 0.96 | 0.20 | 44.8 | 1.80 |
| Specific surface: | | 37 m²/g | | |

EXAMPLE 3

711.7 g (3.416 mol) of Si(OC$_2$H$_5$)$_4$, 14.0 g (0.085 mol) of n-C$_3$H$_7$-Si(OCH$_3$)$_3$ and 24.3 g (0.085 mol) of Ti(OC$_3$H$_7$)$_4$ were combined in 250 ml of ethanolic HCl solution and first stirred for 4 h with reflux. After this time another 150 ml of ethanol as well as 250 ml of desalinated water were added, and after another 30 min of continued stirring with reflux another 375 ml of desalinated water were added. It was then stirred for another 2 hours with reflux, subsequently cooled down, the solid matter was filtered off, washed with 2 l of water and was elutriated in a 10% ammonia solution. After 24 hours of thermal treatment of the suspension at 150° it was further processed analogously to Example 1 and was ground. 214.3 g (97.3% of theoretical yield) of a dental filling material consisting of polymer units of the Formula $TiO_2 \cdot n\text{-}C_3H_7\text{-}SiO_{3/2} \cdot 40 \, SiO_2$ were obtained.

| Analyses: | % C | % H | % Si | % Ti |
|---|---|---|---|---|
| Theory: | 1.40 | 0.27 | 44.66 | 1.86 |
| Actual: | 1.50 | 0.31 | 44.35 | 1.77 |
| Specific surface: | | 48 m²/g | | |

EXAMPLE 4

704.9 g (3.384 mol) Si(OC$_2$H$_5$)$_4$, 21.0 g (0.085 mol)

$$H_2C=\underset{\underset{CH_3}{|}}{C}-\underset{\underset{O}{\|}}{C}-O-(CH_2)_3-Si(OCH_3)_3$$

and 24.1 g (0.085 mol) Ti(OC$_3$H$_7$)$_4$ were precondensed in 250 ml 1n ethanolic HCl solution for 2 h at reflux temperature. Then another 125 ml ethanol and 250 ml of 10 % ammonia water were added. After 30 min of stirring with reflux it was diluted with 350 ml of water. After further processing analogously to Example 1 220.6 g (97.9 % of theoretical yield) of a dental filling material consisting of units of the formula $$H_2C=\underset{\underset{CH_3}{|}}{C}-\underset{\underset{O}{\|}}{C}-O-(CH_2)_3-SiO_{3/2} \cdot TiO_2 \cdot 40 \, SiO_2$$

were obtained.

| Analyses: | % C | % H | % Si | % Ti |
|---|---|---|---|---|
| Theory | 3.16 | 0.42 | 43.25 | 1.80 |
| Actual: | 3.07 | 0.37 | 42.76 | 1.75 |
| Specific surface: | | 30 m²/g | | |

EXAMPLE 5

To 727.8 g (3.49 mol) of Si(OC$_2$H$_5$)$_4$ were added 2 ml of 1% aqueous ammonia solution and it was stirred for 4 h at 100° C. Simultaneously 2 ml of 1n ethanolic HCl solution were added to 19.0 g (0.07 mol) of (C$_6$H$_5$)$_2$Si(OC$_2$H$_5$)$_2$ and it was also stirred for 4 h at 100° C. Analogously 23.7 g (0.07 mol) of Ti(OC$_4$H$_9$)$_4$ were after addition of 2 ml of 1n ethanolic HCl solution also stirred for 4 h at 100° C. After this time these three precondensates were combined, 300 ml of ethanol as well as 150 ml of H$_2$O were added, and they were stirred with reflux until they congealed. It was diluted with 200 ml of ethanol, stirred for another 2 h with reflux, then decanted, the solid matter was fitered off, washed with 2 l of water and elutriated in HCl solution. After 24 hours of after-treatment at 130° C in the autoclave it was processed analogously to Example 1. 223.2 g (97.5% of theoretic yield) of a dental filling material consisting of units of the formula $TiO_2 \cdot (C_6H_5)_2SiO_{2/2} \cdot 50 \, SiO_2$ were obtained.

| Analyses: | % C | % H | % Si | % Ti |
|---|---|---|---|---|
| Theory: | 4.39 | 0.31 | 43.64 | 1.46 |
| Actual: | 4.16 | 0.25 | 42.91 | 1.31 |
| Specific surface: | | 86 m²/g | | |

EXAMPLE 6

727.8 g (3.49 mol) of Si(OC$_2$H$_5$)$_4$, 22.2 g (0.1165 mol) of CH$_2$=CH—Si(OC$_2$H$_5$)$_3$ and 33.1 g (0.1165 mol) of Ti(OC$_3$H$_7$)$_4$ were combined with each other. 3 ml of 1n acetic acid solution was added to the mixture and it was stirred for 12 hours at 80° C. After this time 400 ml ethanol and 200 ml water were added to the mixture and it was stirred another 3 h with reflux. After further processing according to example 1 221.2 g (96.8% of theoretical yield) of a dental filling material consisting of units of the formula $H_2C=CH-SiO_{3/2} \cdot TiO_2 \cdot 30 \, SiO_2$ were obtained.

| Analyses: | % C | % H | % Si | % Ti |
|---|---|---|---|---|
| Theory: | 1.22 | 0.15 | 44.39 | 2.44 |
| Actual: | 1.10 | 0.10 | 43.97 | 2.30 |
| Specific surface: | | 62 m²/g | | |

II. Preparation of the dental materials according to the invention

To produce the dental masses according to the invention the filling materials of Examples 1 to 4 were ground with a ball mill to an average particle size of between about 3 to 7μm. The fillers were then according to standard procedures silanized with 3-methacryloyloxypropyltrimethoxysilane.

The fillers were in amounts from about 58 to 67% (m/m) added to a monomer matrix as it is usually used for dental plastics. Then initiators were added and the masses were kneaded into homogeneous pastes.

A number of physical characteristics was determined with the help of hardened test bodies prepared from the various pastes and were compared to those of commercially available products and laboratory test products (Table I).

EXAMPLES OF DENTAL MASSES ACCORDING TO THE INVENTION

1. Heat-hardened dental masses according to the invention

The production of the test bodies of the heat-hardened dental masses according to the invention took place in such a way that the masses were pressed into the respective test body molds and were then hardened at 90° C for 30 min in a water bath at 6 atmospheres above atmospheric pressure.

EXAMPLE 1 numbers in weight parts 61.0 filler No. 1
26.7 bis-GMA
11.7 TEDMA
0.4 dibenzoylperoxide

EXAMPLE 2 numbers in weight part 58.0 filler No. 2
29.0 bis-GMA
12.6 TEDMA
0.4 dibenzoylperoxide

EXAMPLE 3 numbers in weight parts 67.0 filler No. 3
23.8 bis-GMA
9.9 TEDMA
0.3 dibenzoylperoxide

EXAMPLE 4 numbers in weight parts 67.0 filler according to Example 4
23.8 bis-GMA
9.9 TEDMA
0.3 dibenzoylperoxide 2. Optically hardening dental masses according to the invention The optically hardening dental mass according to the invention consists of a white paste which is hardened through irradiation with a dental halogen lamp (Translux, Kulzer Company). Irradiation time 100 sec.

EXAMPLE 5 numbers in weight parts 61.0 filler No. 2
26.4 bis-GMA
11.6 TEDMA
25 0.2 camphorquinone
0.1 N,N-dimethyl-p-toluidine

Abbreviations bis-GMA: 2,2-bis-[p-(methacryloyloxy-β-hydroxypropoxy)phenyl]-propane
TEDMA: triethyleneglycol dimethacrylate
Commercially available products with which the dental masses according to the invention are compared in Table 1:

Conventional composites (Estilux, Kulzer Company):

The filler is a silanized lithiumaluminum glass with an average particle size of about 4μm. The filler content is ca. 75% (m/m). Hybrid composites (Degufill H, Degussa)

The filler is silanized barium aluminumsilicate glass with an average particle size of ca. 2μm, which is however 100% finer than 5 μm, as well as silanized, highly dispersed $SiO_2$. The filling degree of glass is about 70% (m/m), that of highly dispersed $SiO_2$ ca. 11% (m/m). This results in a total inorganic filler content of ca. 8% (m/m).

Microfiller composites (Durafill, Kulzer & Co., GmbH)

The filler is silanized, highly dispersed $SiO_2$ with an average particle size between 0.01 to 0.04μm. The filling degree is ca. 50% (m/m).

The hardening of all masses was performed with the Translux lamp (Kulzer Company) and an irradiation time of 40 sec.

Light-hardening laboratory test products =VP
(Numbers in weight parts)

VP1:
75 barium aluminumsilicate glass, silanized (average particle grain size ca. 4 μm)
17 bis-GMA
7.8 TEDMA
0.2 dibenzoylperoxide VP2:
35 bis-GMA
14.5 TEDMA
50 highly dispersed $SiO_2$, silanized (average particle size 0.01–0.04 m)
0.5 dibenzoylperoxide The hardening of these pastes took place analogously to the heat-hardening masses according to the invention.

Testing and evaluation of polishability

Test bodies with a diameter of 15 mm and a thickness of 3 mm were produced from all materials. The surfaces of all test bodies were first evenly sanded with fine sanding paper (600 grit). Then they were polished on a cotton cloth under water with superfine aluminum oxide (average particle size 0.04 μm).

The polishability was evaluated visually and graded with the help of a point scale ranging from 1 to 5 with 1 = dull and 5 = high gloss.

TABLE 1

Characteristics of the Dental Masses According to the Invention in comparison with Commercially Available Products and with Conventional and Microfilled Heat-Hardening Dental Masses

| Eigenschaft | Nr. 1 | Nr. 2 | Nr. 3 | Nr. 4 | Nr. 5 | Estilux | Durafill | Degufill H | VP1 | VP2 |
|---|---|---|---|---|---|---|---|---|---|---|
| Biegefestigkeit [N/mm$^2$] DIN 13 | 100 | 74 | 85 | 107 | 128 | 100 | 62 | 110 | 140 | 65 |
| Biegemodul [N/mm$^2$] DIN | 6000 | 6000 | 6800 | 6600 | 6800 | 9700 | 3200 | 8000 | 11000 | 3900 |
| Druckfestigkeit [N/mm$^2$] | 455 | 470 | 381 | 430 | 410 | 300 | 350 | 320 | 350 | 410 |
| Vickers Härte HV 5 [N/mm$^2$] DIN | 620 | 550 | 710 | 880 | 820 | 660 | 290 | 680 | 660 | 330 |

TABLE 1-continued

Characteristics of the Dental Masses According to the Invention in comparison with Commercially Available Products and with Conventional and Microfilled Heat-Hardening Dental Masses

| Eigenschaft | Nr. 1 | Nr. 2 | Nr. 3 | Nr. 4 | Nr. 5 | Estilux | Durafill | Degufill H | VP1 | VP2 |
|---|---|---|---|---|---|---|---|---|---|---|
| Polierbarkeit | 5 | 5 | 5 | 5 | 5 | 1 | 4 | 3 | 1 | 4 |

Key:
1 characteristic
2 flectional strength
3 flexion module
4 pressure resistance
5 pyramid hardness
6 polishability

We claim:

1. A pasty dental material, able to harden to a high-gloss polishable mass in the presence of an initiator, comprising a polymerizable bonding agent and a fine particle filler, wherein said mass contains a heterosiloxane as filler which comprises units of the formula

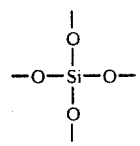  (I)

and units of the formula

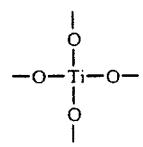  (II)

and optionally contains units of the formula

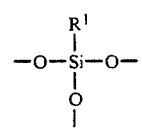  (III)

wherein $R^1$ stands for a linear or branched alkyl group with 1 to 18 carbon atoms, a cycloalkyl group with 5 to 8 carbon atoms, a phenyl group or an arylalkyl group or a linear, optionally branched alkyl group with 1 to 6 carbon atoms bonded with an acrylate or methacrylate residue, or a single olefinic unsaturated, linear, optionally branched hydrocarbon residue with 2 to 8 carbon atoms or a cyclic, single olefinic unsaturated hydrocarbon residue with 5 to 8 carbon atoms, and/or the filler contains units of the formula

wherein $R^2$ is a methyl, ethyl or phenyl group, and the free valances of the oxygen atoms bonded with the silicon or titanium atoms int eh units (I) to (IV) are as in the silica structures saturated by a silicon atom of a same or different unit and/or by a titanium atom, wherein the ratio of the sum of the silicon atoms of the units of Formula (I), (III) and (IV) to the titanium atoms of the units of Formula (II) is 1:1 to 100:1, and the share of silicon atoms of the units (I) to the total amount of silicon atoms is 100 mol% to 30 mol%.

2. The dental material according to claim 1, wherein the filler exists in relation to the units (I) to (IV) as statistical copolycondensate, blockcopolycondensate or as mixtures thereof.

3. The dental material according to claim 1 or 2, wherein the filler is a heterosiloxane which consists only of the units of Formula (I) and (II) whereby the molar ratio of the units of Formula (I) to the units of Formula (II) is 3:1 to 100:1.

4. The dental material according to claim 1 wherein, a heterosiloxane is used as filler which consists of units of Formula (I), (II) and the specific units of Formula (IV)

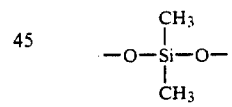

wherein the molar ratio of the units of Formula (I) and (IV) to the units of Formula (II) is 1:1 to 100:1.

5. The dental material according to claim 1 wherein, the heterosiloxane filler has a specific surface of up to 200 m²/g, and a particle size of 0.01 μm to 100μm.

6. The dental material according to claim 5 wherein the surface is 100 m²/g.

7. The dental material according to claim 5 wherein the particle size is 0.1 μm to 30 μm.

8. The dental material according to claim 1, wherein the heterosiloxane filler is used in the dental material in an amount from 20 to 90 wt%.

9. The dental material according to claim 8 wherein the amount is from 40 to 90 wt%.

* * * * *